United States Patent [19]

Snyder

[11] Patent Number: 4,708,813
[45] Date of Patent: Nov. 24, 1987

[54] NONLATHERING CLEANSING MOUSSE WITH SKIN CONDITIONING BENEFITS

[75] Inventor: William E. Snyder, Cincinnati, Ohio

[73] Assignee: The Procter & Gamble Company, Cincinnati, Ohio

[21] Appl. No.: 914,395

[22] Filed: Oct. 2, 1986

Related U.S. Application Data

[63] Continuation-in-part of Ser. No. 765,901, Aug. 14, 1985, abandoned.

[51] Int. Cl.$^4$ .................. C11D 1/72; C11D 3/22; C11D 3/46; C11D 17/04
[52] U.S. Cl. .................... 252/90; 252/89.1; 252/170; 252/173; 252/174.17; 252/174.21; 252/305; 252/DIG. 1; 252/DIG. 5
[58] Field of Search ............ 252/89.1, 90, 170, 174.7, 252/174.21, 173, 305, DIG. 5

[56] References Cited

U.S. PATENT DOCUMENTS

| | | | |
|---|---|---|---|
| 2,655,480 | 10/1953 | Spitzer et al. | 252/90 |
| 3,136,696 | 6/1964 | Harrison | 424/73 |
| 3,666,690 | 5/1972 | Bann | 252/547 |
| 3,818,105 | 6/1974 | Coopersmith | 424/358 |
| 3,923,970 | 12/1975 | Breuer | 424/47 |
| 3,959,160 | 5/1976 | Horsler et al. | 252/90 |
| 3,970,583 | 7/1976 | Hart et al. | 252/305 |
| 4,035,477 | 7/1977 | Schubert | 424/73 |
| 4,088,751 | 5/1978 | Kenhare | 424/73 |
| 4,278,570 | 7/1981 | Flom | 424/170 |
| 4,482,537 | 11/1984 | El-Menshawy | 424/73 |
| 4,491,539 | 1/1985 | Hoskins | 252/541 |
| 4,495,079 | 1/1985 | Good | 514/873 |
| 4,543,205 | 9/1985 | Contamin | 252/106 |

OTHER PUBLICATIONS

Cosmetics & Toiletries, pp. 66–70, 1976, *Nonionic Aerosol Shave Foam* #10, (p. 69).

*Primary Examiner*—Dennis L. Albrecht
*Attorney, Agent, or Firm*—Ronald L. Hemingway; Richard C. Witte

[57] ABSTRACT

A mild skin-cleansing, nonlathering mousse-forming emulsion which leaves the skin, after washing, feeling moisturized, soft and smooth, and which does not require rinsing. The emulsion comprises:

A. from about 95% to about 99.5% of a concentrate containing by weight of the concentrate:
  1. from 1.5% to 15% nonionic surfactant;
  2. from about 0.2% to about 5% of a $C_{12}$–$C_{22}$ saturated, straight chain fatty alcohol;
  3. from about 5% to about 35% of an emollient other than a $C_{12}$–$C_{22}$ fatty alcohol;
  4. from about 5% to about 20% of a skin moisturizer;
  5. the balance water; the weight ratio of surfactant:emollient plus fatty alcohol being from about 0.1:1 to about 0.5:1; and B. from 0.5% to 5% of a moderately water-soluble propellant (e.g., nitrous oxide).

The mousse emulsion is packaged in a pressurized aerosol container.

1 Claim, No Drawings

NONLATHERING CLEANSING MOUSSE WITH SKIN CONDITIONING BENEFITS

CROSS-REFERNCE TO PRIOR APPLICATION

This is a continuation-in-part of application Ser. No. 765,901, filed on Aug. 14, 1985, now abandoned.

TECHNICAL FIELD

The present invention is directed to mild personal skin cleansers. More particularly, this invention is directed to pressurized, nonlathering aerosol mousse skin cleansing compositions comprising surfactants and skin conditioning aids.

BACKGROUND OF THE INVENTION

In pressurized skin cleansing compositions, an aqueous liquid concentrate, generally an aqueous soap solution, is contained in a dispenser equipped with a dispensing head and valve, and pressurized with a normally gaseous propellant, e.g., a low molecular weight hydrocarbon or hydrocarbon mixture or a halohydrocarbon or halohydrocarbon mixture. Upon discharge of the emulsion through the dispensing head, the volatilization of the dispersed liquid droplets of propellant causes the dispensed concentrate to foam. Depending upon the precise formulation of the concentrate, the dispensed product may range from a dense creamy foam to a light foam.

The term "emulsion" will be used throughout this specification and claims to refer to the whole liquid contents of the dispenser, i.e., the emulsion concentrate plus water-soluble propellant, and the term "concentrate" will be used to refer to the liquid contents of the dispenser, other than the propellant, "liquid" in this context embracing solutions, emulsions and suspensions. In other words, the concentrate itself may be an emulsion or suspension and not necessarily a solution of the skin cleansing and conditioning ingredients in a suitable liquid medium, which, in the case of the present invention, will be water. The term "mousse", as used herein, refers to the dispensed product unless otherwise specified.

The cleansing of skin with surface-active cleansing preparations has become a focus of great interest. Many people wash and scrub their skin with various surface-active preparations several times a day. Ideal skin cleansers should cleanse the skin gently, causing little or no irritation, and without defatting and overdrying the skin or leaving it taut after frequent routine use. Most lathering soaps, liquids and bars included, fail in this respect.

Moisturizers such as glycerin provide skin conditioning benefits, and it is known to add moisturizers to skin cleansing products such as toilet bars and liquid and aerosol skin cleansers.

Emollients such as fatty glycerides, mineral oils and fatty alcohols provide smoothness and a protective coating to the skin. The use of these materials in skin cleansing products such as toilet bars, liquid and aerosol skin cleansing products is also known.

Skin cleansing products which produce voluminous lather generally require rinsing from the skin after application thereby resulting in a substantial loss of any moisturizers and/or emollients which may have been formulated into the product for conditioning of the skin.

Skin cleansing products, and in particular aerosol products containing moisturizers and emollients, can be formulated with low lathering, nonionic surfactants so as to reduce the need for rinsing. Such compositions, however, will not necessarily produce a mousse which has a pleasing creamy texture. Such texture is highly desirable for aesthetic reasons in a skin cleansing product.

OBJECT OF THE INVENTION

The object of the present invention is to provide a non-lathering skin cleansing product which has a pleasing creamy texture, does not require rinsing from the skin, and which provides substantial skin conditioning benefits.

SUMMARY OF THE INVENTION

The present invention is a mousse-forming composition for skin cleansing. The mousse has a rich, creamy texture, provides significant conditioning benefits to the skin, and does not require rinsing.

The composition comprises:

A. from about 95% to about 99.5% of a concentrate, containing by weight of said concentrate:
  1. from about 1.5% to about 15% of one or more nonionic surfactants selected from ethoxylated nonionic surfactants, partially or wholly esterified polyols and mixtures thereof, having an HLB of from about 7 to about 18;
  2. from about 0.2% to about 5% of a $C_{12}-C_{22}$ saturated, straight chain fatty alcohol;
  3. from about 5% to about 35% of an emollient other than a $C_{12}-C_{22}$ saturated, straight chain fatty alcohol;
  4. from about 5% to about 20% of a skin moisturizer;
  5. the balance water; the weight ratio of surfactant: emollient plus $C_{12}-C_{22}$ saturated, straight chain fatty alcohol being from about 0.1:1 to about 0.5:1; and B. from about 0.5% to about 5% water-soluble propellant gas, by weight of the total emulsion composition, the said propellant gas having a solubility in water of 15 ml to 1000 ml per liter at one atmosphere and 70° F. (21.1° C.), and having a vapor pressure equal to or greater than about 8788 g per sq. cm. gauge at 21.1° C.

DETAILED DESCRIPTION OF THE INVENTION

The invention relates to a skin cleansing mousse, packaged in a pressurized aerosol dispenser, which provides superior skin conditioning benefits. The composition is nonlathering, and therefore does not require rinsing from the skin after application. The no-rinse feature results in maximum retention on the skin of the skin conditioning ingredients present in the mousse composition. The mousse has a rich creamy texture when dispensed from the aerosol dispenser. After application to the skin, any excess is easily wiped off (e.g., with a tissue or cloth), leaving a substantial residue of skin conditioning ingredients (moisturizers and emollients) on the skin. This is in contrast to high lathering mousse compositions which require rinsing. In the act of rinsing, substantial proportions of the skin conditioning ingredients which have been applied to the skin with the mousse are taken up into the rinse water and are thus wasted.

The emulsion compositions of the present invention comprise:

A. from about 95% to about 99.5% of a concentrate, containing by weight of the concentrate:
1. from about 1.5% to about 15% of one or more nonionic surfactants selected from ethoxylated nonionic surfactants and partially or wholly esterified polyols (or mixtures of such surfactants) having an HLB of from about 7 to about 18;
2. from about 0.2% to about 5% of a $C_{12}$–$C_{22}$ saturated, straight chain fatty alcohol;
3. from about 5% to about 35% of an emollient other than a $C_{12}$–$C_{22}$ saturated, straight chain fatty alcohol;
4. from about 5% to about 20% of a skin moisturizer;
5. the balance water; the weight ratio of surfactant: emollient plus $C_{12}$–$C_{22}$ saturated, straight chain fatty alcohol being from about 0.1:1 to about 0.5:1; and B. from about 0.5% to about 5% water-soluble propellant gas, by weight of the total emulsion composition, the said propellant gas having a solubility in water of from about 15 ml to about 1000 ml per liter at one atmosphere and 21.1° C., and having a vapor pressure equal to or greater than 8788 g per sq. cm. gauge at 21.1° C.

All percentages and proportions herein are "by weight" unless specified otherwise.

Fatty Alcohol Foam Modifier

The $C_{12}$–$C_{22}$ saturated, straight chain fatty alcohols of the present invention perform two functions. They enhance the stability of the dispensed mousse, thereby contributing to the creamy, rich foam which is highly desirable. They also provide an emollient effect on the skin. Examples of specific fatty alcohols useful for this combined function in the present composition are cetyl alcohol, stearyl alcohol and lauryl alcohol, as well as mixtures thereof.

The level of $C_{12}$–$C_{22}$ saturated, straight chain fatty alcohol in the compositions herein is from about 0.2% to about 5%, preferably from about 1% to about 4%. The preferred alcohol is cetyl at a level of from about 1% to about 3%.

Emollients

The emollients of the present invention are water-insoluble, oily or waxy materials which coat the skin with an occlusive layer and thereby act as a barrier to retard loss of water from the skin. Such materials have been used extensively in the cosmetic art. Representative examples include petrolatum, mineral oil, beeswax, silicone oil, lanolin and oil-soluble lanolin derivatives, fatty oxyesters such as myristylethoxy(3)palmitate and ethylhexyloxystearate, and hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, castor oil, soybean oil, avocado oil, safflower oil, coconut oil. hazelnut oil, olive oil and sunflower seed oil. Fatty alcohols other than the $C_{12}$–$C_{22}$ saturated, straight chain fatty alcohols can be used as the emollient element of the present compositions. Examples of such alcohols are palmitoleyl, oleyl, lignoceryl, and ximinic alcohols. Preferred emollients are mineral oil, myristylethoxy(3)palmitate and ethylhexyloxystearate.

The amount of emollient in the aqueous concentrate is from about 5% to about 35%, preferably from about 10% to about 30%, and most preferably from about 15% to about 25%. The total amount of emollient plus $C_{12}$–$C_{22}$ saturated, straight chain fatty alcohol should be such that the weight ratio of surfactant to emollient plus $C_{12}$–$C_{22}$ saturated, straight chain fatty alcohol is from about 0.1:1 to about 0.5:1.

Skin Moisturizers

Skin moisturizers are hygroscopic substances which, when present on the skin, help retain water and make this water available on the stratum corneum so as to alter its physical properties and produce a desirable softness and suppleness in the texture of the skin. Typical moisturizers are $C_2$–$C_6$ polyhydric alcohols, e.g., glycerin, propylene glycol, sorbitol, etc., and polyethylene glycols having molecular weights of from about 100 to about 1500. The preferred moisturizer is glycerin. Moisturizers comprise from about 5% to about 20% of the aqueous concentrate, preferably from about 7% to about 15% and most preferably from about 7% to about 12%.

Surfactant

The surfactants of the present invention are nonionic surfactants selected from ethoxylated nonionic surfactants and wholly or partially esterified polyols. These nonionic surfactants provide skin cleansing benefits and act as the emulsifying agents to maintain a uniform dispersion of the emollient and other ingredients in the composition. These surfactants when formulated into the present composition also produce a dense, creamy mousse when the composition is dispensed from the aerosol container, thereby providing a composition which can be applied to the skin without a requirement for subsequent aqueous rinsing. Solutions of these surfactants, when subjected to shear, do not foam or bubble appreciably.

The ethoxylated nonionic surfactants can be broadly defined as compounds produced by the condensation of ethylene oxide groups (hydrophillic in nature) with an organic hydrophobic compound, which may be aliphatic or alkyl aromatic in nature. The length of the hydrophilic or polyoxyethylene radical which is condensed with any particular hydrophobic group can be readily adjusted to yield a water-soluble compound having the desired degree of balance between hydrophilic and hydrophobic elements.

Representative examples of ethoxylated nonionic surfactants are the following:

(1) Compounds formed by condensing ethylene oxide with a hydrophobic base formed by the condensation of propylene oxide with propylene glycol. The hydrophobic portion of the molecule which, of course, exhibits water insolubility, has a molecular weight of from about 1500 to 1800. The addition of polyoxyethylene radicals to this hydrophobic portion tends to increase the water solubility of the molecule as a whole and the liquid character of the product is retained up to the point where the polyoxyethylene content is about 50% of the total weight of the condensation product. These surfactants are sold under the tradename Pluronics® by BASF Wyandotte Corp.

(2) The polyethylene oxide condensates of alkyl phenols, e.g., the condensation products of alkyl phenols having an alkyl group containing from about 6 to about 12 carbon atoms in either a straight chain or branched chain configuration with ethylene oxide, the said ethylene oxide being present in amounts equal to 5 to 25 moles of ethylene oxide per mole of alkyl phenol. The alkyl substituent in such compounds may be derived from polymerized propylene, diisobutylene, octene, or nonene, for example. Representative examples of these surfactants are sold under the name Igepal ® by GAF Corporation.

(3) Compounds derived from the condensation of ethylene oxide with the product resulting from the reaction of propylene oxide and ethylene diamine. For example, compounds containing from about 40% to about 80% polyoxyethylene by weight and having a molecular weight of from about 5,000 to about 11,000 resulting from the reaction ethylene oxide groups with a hydrophobic base constituted of the reaction product of ethylene diamine and excess propylene oxide, said base having a molecular weight of the order of 2,500 to 3,000 are satisfactory. Representative examples of this class of nonionic surfactants are sold under the name Alkatronic ® by Alkaril Chemical Co.

(4) The condensation product of aliphatic alcohols having from 8 to 22 carbon atoms, in either straight chain or branched chain configuration, with ethylene oxide, e.g., a coconut alcoholethylene oxide condensate having from 5 to 30 moles of ethylene oxide per mole of coconut alcohol, the coconut alcohol fraction having from 10 to 14 carbon atoms. Representative examples of this class of nonionic surfactants are sold under the name Alkasurf ® by Alkaril Chemical Co.

(5) Condensation products of ethylene oxide with $C_{10}$–$C_{22}$ fatty acid esters of sorbitan. Representative examples of this class of nonionic surfactant are sold under the name Tween ® by ICI Americas, Inc.

(6) Condensation products of ethylene oxide with the $C_{10}$–$C_{22}$ fatty acid esters of methyl glucosides. Representative examples of this class of nonionic surfactant are sold under the name Glucamate ® by Amerchol Corp.

(7) Condensation products of ethylene oxide with $C_{10}$–$C_{22}$ fatty acids. Representative examples of this class of nonionic surfactant are sold under the name Nopalcol by Diamond Shamrock Company.

The wholly or partially esterified polyol surfactants herein are the product of the esterification of all or less than all of the free hydroxyl groups of a polyol with a carboxylic acid, typically a fatty acid having from about 8 to about 22 carbon atoms. The polyols used in preparing such surfactants typically contain from 2 to about 6 hydroxyl groups. Typical polyols include ethylene glycol, glycerol, pentaerythritol, and carbohydrates such as glucose, sucrose, methylglucose, sorbitol and dehydration products of carbohydrates such as sorbitan, which is the dehydration product of sorbitol. Examples of these surfactants are ethyleneglycol monostearate, ethyleneglycol distearate, glycerol monopalmitate, sucrose distearate, sucrose octapalmitate, propyleneglycol distearate, sorbitan monostearate and methylglucoside sesquistearate.

The nonionic surfactant (or mixture of nonionic surfactants) should be chosen so as to have an HLB of from about 7 to about 18. Mixtures of individual surfactants whose HLB's lie outside the 7–18 range can be used, so long as the HLB of the mixture lies within this range. An HLB within this range provides emulsion stability in the composition and good skin cleansing performance.

Preferred compositions herein generally contain a mixture of ethoxylated nonionic surfactants and partially esterified polyol surfactant.

A listing of nonionic surfactants, their commercial sources and the HLB values can be found in *McCutcheon's Detergents and Emulsifiers, North American Ed.* 1984, published by McCutcheon Division, McPublishing Co., Glen Rock, N.J., 07452, incorporated by reference herein.

The compositions herein should be substantially free of anionic surfactants (including soap) and other types of nonionic surfactants (e.g., amine oxides, fatty acid amides, etc.). These materials tend to give the mousse a foaming consistency which is not desirable for use in a no-rinse mode. Cationic surfactants are also preferably avoided in the composition herein.

The nonionic surfactants are present in the concentrate at levels of from about 1.5% to about 15%, preferably from about 3% to about 9%. The weight ratio of surfactant:emollient plus $C_{12}$–$C_{22}$ saturated, straight chain fatty alcohol should be between about 0.1:1 and about 0.5:1.

Propellant

The propellants used in the aerosol compositions herein are moderately water-soluble gases and are present in the emulsion composition at levels of from 0.5% to about 5%. By "moderately water-soluble" is meant that the gas has a solubility in water of from about 15 ml to about 1000 ml per liter, measured at one atmosphere pressure and 70° F. (21.1° C.). The gas should have a vapor pressure at 21.1° C. equal to or greater than 125 psig (8788 g per sq. cm. gauge). Examples of suitable propellants are nitrous oxide, carbon dioxide, and nitrogen.

The compositions are preferably substantially free of water-insoluble propellants, e.g., hydrocarbon and halohydrocarbon gases, such as Freons and isobutane.

The composition is packaged in a valved container that is designed to maintain the composition under pressure and to dispense it upon opening of the valve.

Optional Ingredients

The compositions of the invention can optionally contain dyes, perfumes, antioxidants, antimicrobials, viscosity modifiers, skin protective agents such as allantoin, and other auxiliary materials which are conventionally used in cosmetic compositions.

The compositions should have a pH of from about 4.5 to about 8.5. Depending upon the other ingredients which may be selected for use in the composition, adjustment of pH to within this range with conventional pH adjustment agents (e.g., citric acid, sodium hydroxide) may be necessary.

A particularly preferred optional ingredient is a cationic or nonionic polymeric skin feel acid. Reduced skin irritation benefits of both types of polymers are set out in "Polymer JR for Skin Care" Bulletin, by Union Carbide, 1977. The cationics are preferred over the nonionic because they provide better skin feel benefits. Examples of the cationic polymers and the nonionic polymers useful for this purpose are set out below.

The amount of polymeric skin feel acid found useful in the concentrate is from about 0.05% to about 5%, preferably from about 0.1% to about 2%, and more preferably 0.1% to 1.0%.

A particularly preferred skin feel acid is cationic (quaternized) guar gum, e.g., Jaguar C-14-S, from Celanese Corp.

Other types of high molecular weight polymeric skin feel agents, such as nonionic guar gums, Merquats 100 and 550, made by Merck & Co., Inc; UCARE Polymer JR-400, made by Union Carbide Corp.; Mirapol A15 made by Miranol Chemical Company, Inc.; and Galactasol 811, made by Henkel, Inc.; plus others, are usable.

The nonionic polymers found to be useful as skin feel aids include the nonionic polysaccharides, e.g., nonionic hydroxypropyl guar gums, offered by Celanese Water Soluble Polymers, a Division of Celanese Corp. A preferred nonionic hydroxypropyl guar gum material is Jaguar ® HP-60 having hydroxypropyl molar substitution of about 0.6. Another class of useful nonionics is the cellulosic nonionic polymers, e.g., hydroxyethylcellulose and carboxymethylcellulose.

The invention will be illustrated by the following example.

EXAMPLE 1

A composition of the invention is prepared containing 98 parts of Emulsion Concentrate A (below) and 2 parts of nitrous oxide propellant.

| Emulsion Concentrate (A) | |
|---|---|
| Semtol 70 M.O.[1] | 11.00% |
| Cetyl alcohol | 2.40 |
| Ethylhexyloxystearate | 2.10 |
| (Wickhen Chemical Co.) | |
| Amerchol L-101[2] | 5.00 |
| Glucamate SSE-20[3] | 3.10 |
| Glucate SS[4] | 1.00 |
| Myristylethoxy(3)palmitate | 1.40 |
| (Scher Chemical Co.) | |
| Carbopol 1342[5] | 0.10 |
| Glycerin | 7.50 |
| Methyl paraben | 0.20 |
| Propyl paraben | 0.10 |
| Potassium hydroxide (45% in H$_2$O) | 0.20 |
| Na$_4$ EDTA | 0.10 |
| Germall 115 | 0.10 |
| Allantoin | 0.40 |
| FD&C Red #4 (1% in H$_2$O) | 0.20 |
| FD&C Yellow #5 (1% in H$_2$O) | 0.04 |
| Perfume | 0.18 |
| Water[6] | to 100 |

[1]Mineral Oil (Sonneborn Division of Witco Chemical Co.)
[2]10% solution of lanolin alcohols in mineral oil (Amerchol Corp.)
[3]Condensation product of 20 moles of ethylene oxide with methyl glucoside sesquistearate (Amerchol Corp.) HLB = 15
[4]Methyl glucoside sesquistearate (Amerchol Corp.) HLB = 6
[5]Water-soluble polymeric thickener (B. F. Goodrich Co.)
[6]Water purified by double reverse osmosis The composition is prepared by the following procedure:

A water phase is prepared by mixing the water, Carbopol 1342, glycerin, methyl paraben and propyl paraben together. A separate oil phase is prepared by mixing the mineral oil, cetyl alcohol, ethylhexyloxystearate, Amerchol L-101, myristylethoxypalmitate, Glucamate SSE-20 and Glucate SS together at 180° F. (82.2° C.).

The oil phase is then pumped into the water phase at 160°–210° F. (71.1°–98.9° C.). The potassium hydroxide and Na$_4$ EDTA are then added to this mixture while maintaining the temperature at about 180° F. (82.2° C.). The mixture is then cooled to about 120° F. (49° C.) by circulation through a heat exchanger or jacket cooled mix tank. As the mixture is being cooled to 120° F. (49° C.), the Germall 115 is added at about 140° F. (60° C.), the allantoin and FD&C dyes are added at about 125° F. (51.7° C.) and the perfume is added at 120° F. (49° C.). The finished emulsion concentrate is then subjected to continuous mixing while being pumped through a heat exchanger to cool to room temperature.

The cooled emulsion concentrate is then filled into aluminum cans. Aerosol activator assemblies are then crimped onto the cans to form a tight seal. Pressurized nitrous oxide is then pumped into the cans in an amount sufficient to provide a composition consisting of 2% nitrous oxide and 98% emulsion concentrate in each can.

Upon activation of the aerosol assembly, the composition is dispensed under pressure in the form of a creamy, nonfoaming mousse which can be applied to the skin to effect simultaneous cleansing and conditioning of the skin. Excess composition can be cleanly wiped from the skin with no need to rinse.

What is claimed is:

1. A mousse-forming aerosol skin cleansing composition comprising:
   A. from about 95% to about 99.5% of a concentrate, containing by weight of the concentrate:
   1. from about 3% to about 9% of a mixture of methyl glucoside sesquistearate and the condensation product of about 20 moles of ethylene oxide with one mole of methyl glucoside sesquistearate, the said mixture having an HLB of from about 7 to about 18;
   2. from about 1% to about 3% of cetyl alcohol;
   3. from about 15% to about 25% of an emollient selected from the group consisting of mineral oil, ethylhexyloxystearate, myristyloxy(3)palmitate, lanolin alcohols and mixtures thereof;
   4. from about 7% to about 15% glycerin;
   5. the balance water; the weight ratio of Component (1.) to Component (2.) plus Component (3.) being from about 0.1:1 to about 0.5:1; and
   B. from about 0.5% to about 5% nitrous oxide said composition being contained in a pressurized aerosol dispenser.

* * * * *